US008486139B2

(12) United States Patent
Kishida et al.

(10) Patent No.: US 8,486,139 B2
(45) Date of Patent: Jul. 16, 2013

(54) METHOD OF PREPARING DECELLULARIZED SOFT TISSUE, GRAFT AND CULTURE MATERIAL

(75) Inventors: Akio Kishida, Tokyo (JP); Tsuyoshi Kimura, Tokyo (JP); Hisatoshi Kobayashi, Tsukuba (JP); Toshiya Fujisato, Suita (JP)

(73) Assignees: National University Corporation Tokyo Medical and Dental University, Tokyo (JP); National Cerebral and Cardiovascular Center, Osaka (JP)

( * ) Notice: Subject to any disclaimer, the term of this patent is extended or adjusted under 35 U.S.C. 154(b) by 315 days.

(21) Appl. No.: 12/530,510

(22) PCT Filed: Mar. 7, 2008

(86) PCT No.: PCT/JP2008/054207
§ 371 (c)(1),
(2), (4) Date: Feb. 25, 2010

(87) PCT Pub. No.: WO2008/111530
PCT Pub. Date: Sep. 18, 2008

(65) Prior Publication Data
US 2010/0145444 A1   Jun. 10, 2010

(30) Foreign Application Priority Data
Mar. 9, 2007   (JP) ................................. 2007-061025

(51) Int. Cl.
*A61F 2/14* (2006.01)
(52) U.S. Cl.
USPC ........................................................ 623/5.11
(58) Field of Classification Search
USPC .................... 623/5.11, 5.16, 23.72
See application file for complete search history.

(56) References Cited

U.S. PATENT DOCUMENTS

| 2003/0087428 A1 | 5/2003 | Wolfinbarger, Jr. et al. |
| 2006/0110720 A1* | 5/2006 | Fujisato et al. ............... 435/1.1 |

FOREIGN PATENT DOCUMENTS

| EP | 1 541 157 A1 | 6/2005 |
| EP | 1 698 358 A1 | 9/2006 |
| WO | 01/49210 A1 | 7/2001 |
| WO | 2004/024170 A1 | 3/2004 |
| WO | 2005/063316 A1 | 7/2005 |

OTHER PUBLICATIONS

Kimura, T., et al., "Preparation of decellularized cornea as artificial cornea", Annual Report of the Institute of Biomaterials and Bioengineering, Tokyo Medical and Dental University, Mar. 3, 2007, vol. 40, p. 16-19.
International Search Report to PCT/JP2008/054207, dated Apr. 1, 2008.
Funamoto, Seiichi, et al., "The use of high-hydrostatic pressure treatment to decellularize blood vessels", Biomaterials, vol. 31, 2010, pp. 3590-3595.
Hashimoto, Yoshihide, et al., "Preparation and characterization of decellularized cornea using high-hydrostatic pressurization for corneal tissue engineering", Biomaterials, vol. 31, 2010, pp. 3941-3948.
Supplementary European Search Report issued to Application No. EP 08 72 1624, Date of Completion of Search: Oct. 23, 2012.

* cited by examiner

*Primary Examiner* — William H Matthews
(74) *Attorney, Agent, or Firm* — Hoffmann & Baron, LLP

(57) ABSTRACT

It is intended to provide a method of preparing a decellularized soft tissue whereby swelling after an ultrahigh pressure treatment can be inhibited, etc. The above-described method of preparing a decellularized soft tissue comprises the application step wherein an ultrahigh hydrostatic pressure is applied to an isolated soft tissue in a medium to thereby disrupt cells in the soft tissue, and the removal step wherein the disrupted cells are removed. As the medium, use is made of an aqueous solution containing a water-soluble polysaccharide such as dextran.

4 Claims, 10 Drawing Sheets (A) UNPROCESSED CORNEA

EPITHELIUM ANTERIUS CORNEAE

PARENCHYMA

ENDOTHELIUM CAMERAE ANTERIORIS (B) DECELLULARIZED CORNEA (A) UNPROCESSED CORNEA

EPITHELIUM ANTERIUS CORNEAE

PARENCHYMA

ENDOTHELIUM CAMERAE ANTERIORIS (B) DECELLULARIZED CORNEA (c) THREE WEEKS AFTER PROCEDURE (b) TWO WEEKS AFTER PROCEDURE (a) ONE WEEK AFTER PROCEDURE

METHOD OF PREPARING DECELLULARIZED SOFT TISSUE, GRAFT AND CULTURE MATERIAL

CROSS-REFERENCE TO RELATED APPLICATIONS

This application claims priority to PCT/JP2008/054207 which was filed Mar. 7, 2008, which claims priority to JP 2007-061025 filed on Mar. 9, 2007 the contents of which are incorporated by reference herein in their entireties.

TECHNICAL FIELD

The present invention relates to a graft for transplantation into an animal and a method of preparing soft tissue adapted to the graft.

BACKGROUND ART

Up to date, a method of chemical processing of living tissue using a fixing agent such as glutaraldehyde or a method of removing cellular components from living tissue have been widely applied and found clinical application as methods of preparing a graft for transplantation into an animal.

It has been estimated for example that there are in excess of one million patients worldwide requiring a corneal graft. However as a result of a shortage of available eye balls in many countries, the number of patients undergoing corneal transplants annually is only about 60,000 persons. In Japan, in contrast to approximately 5000 wait-listed transplant candidates registered with the Japan Eye Bank Association, the number of eye donors is approximately 1000 and the number of usable eye balls is approximately 1500.

Moreover, since current corneal transplantation therapies employ allogeneic transplantation of the cornea of another person, there are problems associated with rejection reactions depending on the underlying disease. In this context, the development of an artificial cornea is expected to provide a radical solution to the above problems.

Synthetic polymers such as polymethylmethacrylate (PMMA), polytetrafluoroethylene (PTFE) and polyvinylalcohol (PVA) have been tested as materials for an artificial cornea. However the low compatibility between these materials and corneal tissue sometimes results in detachment or infection at the junction site of the artificial cornea and the corneal tissue.

Techniques of improving compatibility with living tissue have been developed in recent years by using a graft of decellularized tissue as a residual supporting tissue after removal of cells from living tissue. This decellularized tissue displays excellent compatibility with living tissue when compared with synthetic polymers as a result of physical properties which resemble living tissue.

Current cell depletion methods include chemical methods applying a chemical solution containing a surfactant or a proteolytic enzyme to living tissue or ultrahigh pressure treatment applying ultrahigh pressure of more than 5000 atmospheres to living tissue in water (refer to Patent Document 1). The latter method is used to solve problems associated with the former method such as the fact that infection is not always prevented and chemicals must be removed after transplantation Patent Document 1: Pamphlet of WO2004/24170.

DISCLOSURE OF THE INVENTION

Problems to be Solved by the Invention

However when the methods disclosed in Patent Document 1 are used on living tissue such as soft tissue, there is the problem that the considerable tissue swelling after ultrahigh pressure treatment has an adverse effect on tissue characteristics.

The present invention is proposed in view of the above problems and has the object of providing a method of preparing decellularized soft tissue enabling inhibition of swelling after ultrahigh pressure treatment, a graft formed from decellularized soft tissue and a culture material including the decellularized soft tissue.

Means for Solving the Problems

The present inventors completed the present invention by gaining the insight that tissue swelling could be inhibited by applying an ultrahigh hydrostatic pressure to soft tissue in an aqueous solution containing a water-soluble polysaccharide. The present invention is described in further detail hereafter.

(1) A method of preparing a decellularized soft tissue in which soft tissue of animal origin is decellularized, the method including:

an application step of disrupting cells in the soft tissue by applying an ultrahigh hydrostatic pressure to an isolated soft tissue in a medium; and a removal step of removing the disrupted cells, in which the medium is an aqueous solution containing a water-soluble polysaccharide.

(2) The method according to (1) in which the water-soluble polysaccharide is at least one type of polysaccharide selected from a group consisting of dextran, alginic acid, hyaluronic acid, trehalose, 2-methacryloyloxyethyl phosphorylchloine, and polyvinylpyrrolidone.

According to invention (1) or (2), a decellularized soft tissue is obtained by disrupting cells in the soft tissue in the application step and removing the disrupted cells in the removal step.

Since the medium used in the application step is an aqueous solution containing a water-soluble polysaccharide, soft-tissue swelling after the application of ultrahigh pressure processing can be inhibited.

(3) The method according to (1) or (2) in which the ultrahigh hydrostatic pressure is at least 1000 atmospheres.

When the pressure applied to the soft tissue is insufficient, disruption of normal flora existing in the soft tissue is insufficient thereby resulting in a risk of normal flora remaining in the prepared decellularized soft tissue.

According to the invention in (3), since the ultrahigh hydrostatic pressure is at least 1000 atmospheres, sufficient disruption of normal flora occurs thereby inhibiting residual normal flora in the decellularized soft tissue. As a result, safety is improved.

(4) The method according to any one of (1) to (3) in which the application step includes a temperature maintenance step of maintaining a temperature of the medium to be greater than or equal to a melting point of the medium at the ultrahigh hydrostatic pressure.

According to the invention in (4), since the temperature of the medium is maintained to a temperature greater than or equal to the melting point at the ultrahigh hydrostatic pressure, solidification of the medium is inhibited even under a condition of pressurization to an ultrahigh hydrostatic pressure. In this manner, damage to the structure and properties of the decellularized tissue is inhibited.

(5) The method according to any one of (1) to (4) in which the application step includes a pressure limiting step of preventing the applied pressure applied to the medium from taking a value greater than or equal to the melt pressure of the medium.

According to the invention in (5), since the applied pressure is adjusted to a pressure less than the melt pressure of the medium, solidification of the medium during pressure increase or pressure decease in the application step is inhibited. In this manner, damage to the structure and properties of the decellularized tissue is inhibited.

(6) The method according to any one of (1) to (5) in which the soft tissue is corneal tissue.

Since swelling of the decellularized tissue of corneal origin has an adverse effect on the tissue optical transparency, usefulness after transplantation to an animal is reduced.

According to the invention in (6) above, since cornea is used as the soft tissue, swelling in the decellularized tissue of corneal origin can be inhibited. In this manner, usefulness after transplantation to an animal can be improved.

(7) A graft transplanted to an animal, the graft including decellularized soft tissue prepared using the method stated in any one of (1) to (6).

(8) The graft according to (7) further including contiguous tissue positioned on the decellularized soft tissue and adjacent to the soft tissue in the animal body.

(9) A culture material provided with decellularized soft tissue prepared using the method according to any one of (1) to (6) and used for culturing cells in contiguous tissue adjacent to the soft tissue in the animal body.

Effects of the Invention

According to the present invention, decellularized soft tissue is obtained by disrupting cells in soft tissue in an application step and removing the disrupted cells in a removal step. Since the medium used in the application step is an aqueous solution containing a water-soluble polysaccharide, soft-tissue swelling after the application of ultrahigh pressure processing can be inhibited.

PREFERRED MODE FOR CARRYING OUT THE INVENTION

Figure 1:
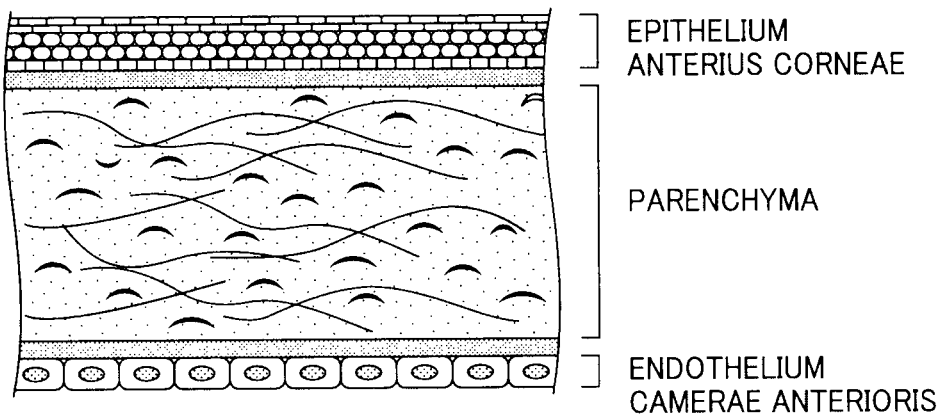
FIG. 1 is a schematic view showing decellularized tissue prepared using a preparation method according to an embodiment of the present invention.
Figure 1:
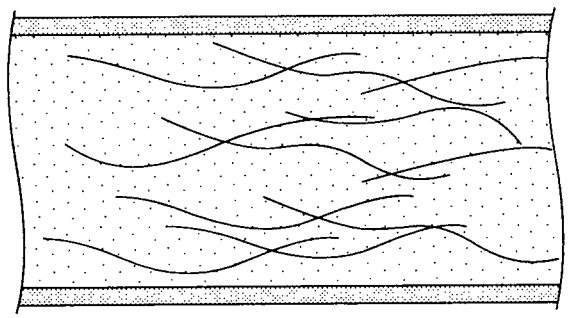

The embodiments of the present invention will be described below. However it is not intended that the invention is limited by the embodiments.

Preparation Method

The preparation method for decellularized tissue according to the present invention includes an application step and a removal step. The details of the respective steps will be described below.

Application Step

The application step disrupts cells in soft tissue by applying an ultrahigh hydrostatic pressure to isolated soft tissue in a medium. There is no particular limitation on the soft tissue used and it may include, for example, cornea, ligament, tracheal tissue, cardiac tissue, amniotic tissue and skin.

The ultrahigh hydrostatic pressure is a hydrostatic pressure enabling disruption of normal flora cells existing in soft tissue and, more precisely, is preferably a pressure of at least 1000 atmospheres. The ultrahigh hydrostatic pressure is more preferably at least 4000 atmospheres from the point of enabling disruption of bacteria existing in soft tissue and, still more preferably, at least 6000 atmospheres from the point of enabling disruption of viruses.

The medium used in the present invention is an aqueous solution containing a water-soluble polysaccharide. Considerable inhibition of tissue swelling after the application step is enabled by application of the ultrahigh hydrostatic pressure in the medium.

There is no particular limitation on the water-soluble polysaccharide and for example, it may include dextran, alginic acid, hyaluronic acid, trehalose, 2-methacryloyloxyethyl phosphorylchloine, polyvinylpyrrolidone. The water-soluble polysaccharide may be used either singly or in combination.

The concentration of the water-soluble polysaccharide in the aqueous solution may be suitably set to inhibit a level of swelling to an allowable range in response to the type of soft tissue used or the applied ultrahigh hydrostatic pressure value. For example, when using a corneal as soft tissue, the polysaccharide concentration (for example of dextran) may be normally greater than or equal to 1 mass % and less than or equal to 10 mass %.

The actual details of the step, for example, include filling a bag formed from a water-impermeable film with an aqueous solution containing a water-soluble polysaccharide and moistening the soft tissue with the aqueous solution. Care must be taken to ensure that air does not remain in an inner portion and the bag is tightly sealed. The bag is placed in a chamber of an ultrahigh hydrostatic pressure processing device (for example "Dr. CHEF (die-type) (Kobe Steel Ltd.) and the device is operated.

During the application step, although there is no particular limitation as along as desired cell disruption characteristics are obtained, and normally 10-30 minutes is sufficient.

Temperature Maintenance Step

It is preferred that the application step includes a temperature maintenance step and in the temperature maintenance step, the temperature of the medium is maintained to greater than or equal to the melting point of the medium under ultrahigh hydrostatic pressure. In this manner, solidification of the medium is inhibited even under pressurization to an ultrahigh hydrostatic pressure and damage to the structure and properties of the prepared decellularized tissue is inhibited.

Since there is a risk of an adverse effect on the structure or properties of the prepared decellularized tissue when the temperature of the medium is too high, normally the temperature of the medium is 25° C.-40° C. and is preferably approximately 30° C.

The actual details of the step include firstly the calculation of the melting point of the medium at a preset ultrahigh hydrostatic pressure using the composition of the medium. The ultrahigh hydrostatic processing device may be controlled so that the internal temperature of the chamber rises to a temperature greater than or equal to the calculated temperature. The temperature of the medium may be fixed to a predetermined value or may vary within a range greater than or equal to the melting point of the medium.

Pressure Limiting Step

The application step preferably includes a pressure limiting step, and in the pressure limiting step, the applied pressure applied to the medium is limited from rising above the melt pressure of the medium. When commencing pressure increase or pressure decrease of the applied pressure, the temperature of the medium undergoes instantaneous and rapid fluctuation. Consequently the structure and properties of the soft tissue may be severely damaged. In the pressure limiting step, the melt pressure is pre-calculated based on the composition of the medium. Rapid fluctuation in the medium temperature is inhibited in particular by reducing the rate of pressure increase or pressure decrease in the applied pressure to equal to or less than a predetermined value. In this manner, solidification of the medium is inhibited during the process of pressure increase or pressure decrease and thus damage to the structure or properties of the decellularized tissue can be inhibited.

Removal Step

The removal step is a step in which disrupted cells are removed. After transplantation, there is a risk of an immunological reaction being induced as a result of a residue of disrupted cells. However such a risk is obviated as a result of the removal step.

There is no particular limitation on the method of removal and washing the tissue in a suitable solution enabling inhibition of adverse effects on the structure or properties of tissue is sufficient. The solution used herein may include an aqueous solution containing a water-soluble polysaccharide, a PBS solution, HEPES buffer solution, MES buffer solution or a known cellular culturing solution. However an aqueous solution containing a water-soluble polysaccharide is preferred from the point of view of enhanced inhibition of swelling.

There is no particular limitation on the method of conserving a decellularized tissue prepared in the above manner as long as a sterile state is obtained and methods include a frozen state, moistened state in a liquid or a dried state. The absence of a limitation on the method of conversation is an advantage of a decellularized tissue according to the present invention.

Graft

The decellularized tissue according to the present invention can be used in a configuration as a graft transplanted into an animal. In other words, a graft according to the present invention is provided with decellularized tissue as described above. The graft may be provided with contiguous tissue on the decellularized tissue. The contiguous tissue is adjacent to the soft tissue which is the source of the decellularized tissue in the animal body. For example, when the soft tissue being the source of decellularized tissue (refer to FIG. 1(B)) is corneal tissue (refer to FIG. 1(A)), the contiguous tissue is the epithelium anterius corneae or the endothelium camerae anterioris.

Culture Material

The decellularized tissue according to the present invention is also useful as a culture material used for culturing cell of the contiguous tissue. In other words, the culturing material of the present invention is provided with the decellularized tissue described above. Cells originating in contiguous tissue are placed onto the decellularized tissue and cultured under suitable conditions thereby enabling cell culture which does not necessarily require the use of special equipment and which inhibits infection. These points indicate a special useful effect in comparison to conventional known culture sheets or amnions.

EXAMPLES

Example 1

Porcine corneas from a pig farm for human consumption was commercially obtained and transported at 4° C. After washing the corneas in PBS solution, the tissue was moistened in a bag formed from polyethylene film filled with a PBS solution containing 3.5 mass % dextran 70 as a medium. The bag was placed in a chamber of "Dr. CHEF" (Kobe Steel Ltd.), a temperature was maintained at 30° C. and a hydrostatic pressure of 4000 atmospheres was applied for 30 minutes (application step). During this time, the "Dr. CHEF" was controlled so that the rate of pressure increase and pressure decrease was respectively 5000 atmospheres/minute (pressure limitation step). Then the cornea after the application step was washed in PBS solution for 72 hours to remove cells in an inner section of the cornea (removal step). A decellularized tissue was prepared in the above manner.

Example 2

A decellularized tissue was prepared using the same steps as Example 1 with the exception that the application pressure was a hydrostatic pressure of 10000 atmospheres.

Example 3

A decellularized tissue was prepared with the same steps as Example 2 with the exception that the medium temperature was 10° C.

Comparative Example 1

The cornea used in Example 1 was immersed for 24 hours at 37° C. in a PBS solution containing 1 w/v % SDS and then immersed for 24 hours in PBS solution. A decellularized tissue was prepared in the above manner.

Comparative Example 2

The cornea used in Example 1 was immersed for 24 hours at 37° C. in a PBS solution containing 1 w/v % "TritonX-100" (registered trademark) and then immersed for 24 hours in PBS solution. A decellularized tissue was prepared in the above manner.

Comparative Example 3

The cornea used in Example 1 was immersed for 24 hours at 37° C. in a PBS solution containing 1 w/v % sodium cholate and then immersed for 24 hours in PBS solution. A decellularized tissue was prepared in the above manner.

Comparative Example 4

Figure 2:
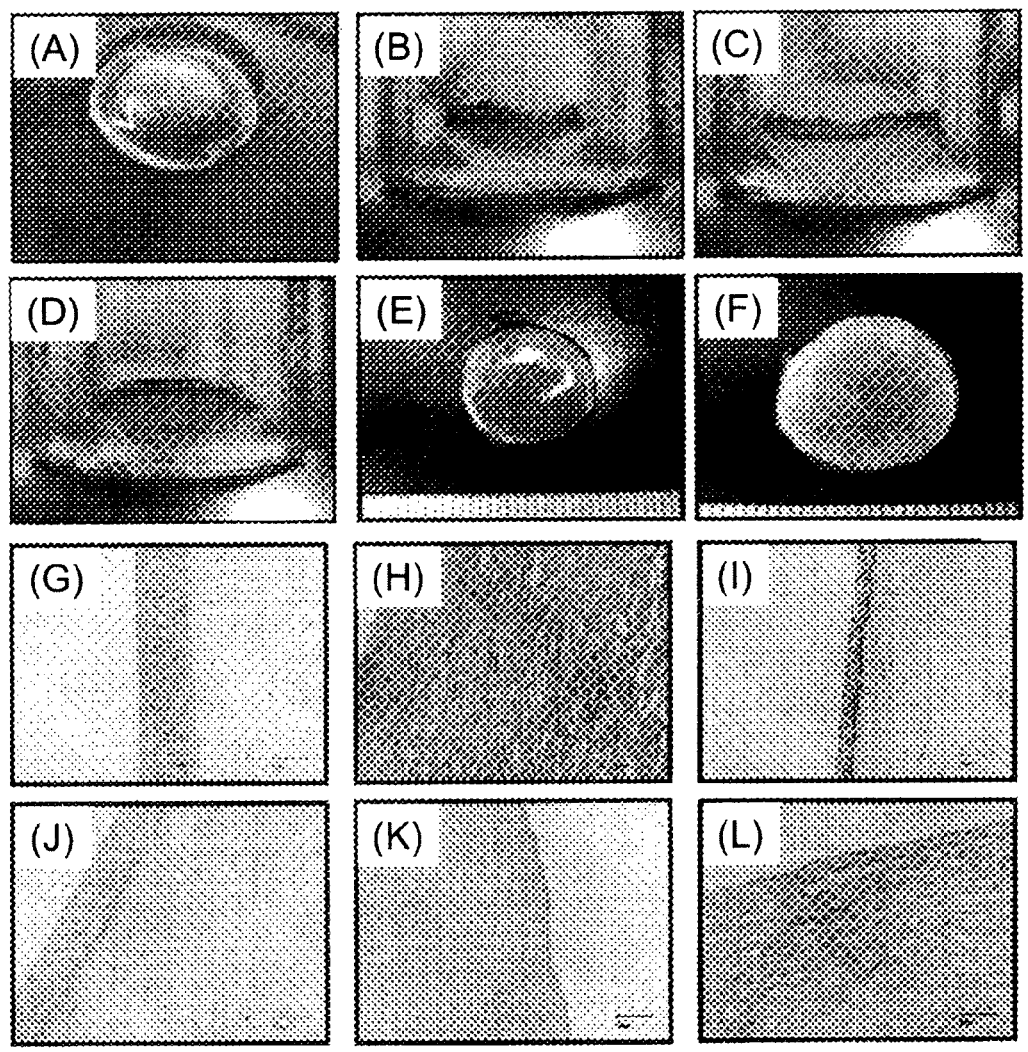
FIG. 2 shows a level of decellularization and a level of swelling in decellularized tissue prepared using a preparation method according to an example of the present invention.
Figure 3:
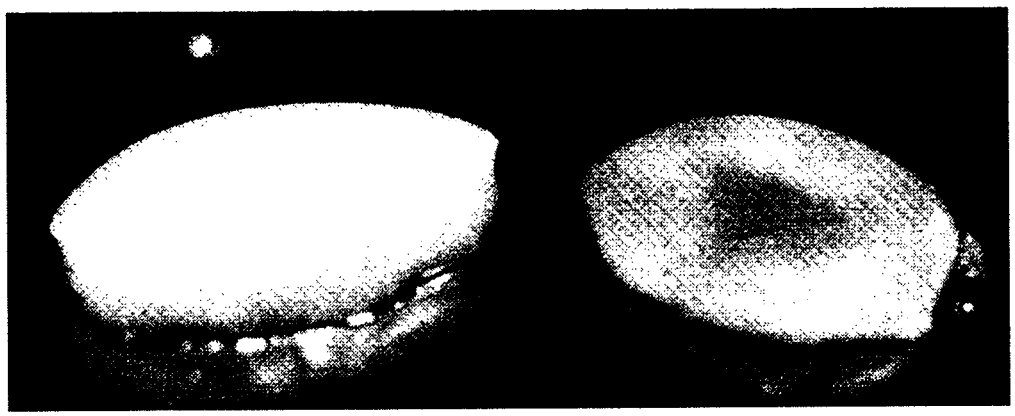
FIG. 3 shows a level of swelling in decellularized tissue prepared using a preparation method according to an example of the present invention.

Instead of the PBS solution containing dextran 70, a PBS solution not containing dextran 70 was used to prepare a decellularized tissue using the same steps as Example 1.
Evaluation
Degree of Swelling The degree of swelling was observed using decellularized tissue prepared in the examples and comparative examples and using a control being a cornea (unprocessed) prior to the application pressure used in the examples. The results are shown in FIG. 2 and FIG. 3. FIG. 2 shows the respective results in which (A) shows the control, (B) shows Comparative Example 1, (C) shows Comparative Example 2, (D) shows Comparative Example 3, (E) shows Example 1, (F) shows Example 2. (A), (E), (F) are top views of the respective decellularized tissue and (B), (C), (D) are side views of the respective decellularized tissue. The left side in FIG. 3 shows the results of Comparative Example 4 and the right side shows the results of Example 1.

As shown in FIG. 2(B)-(D), the decellularized tissue in Comparative Examples 1-3 in which decellularization is performed using chemical processing displays conspicuous swelling and has a membrane width of approximately 3 times that of the control cornea (not shown due to excessive thinness). In contrast, the decellularized tissue according to Example 1 and Example 2 has a membrane thickness of approximately 1.5 times that of the control cornea (not shown). Thus it can be confirmed that decellularization by application of ultrahigh hydrostatic pressure causes a conspicuous inhibition of swelling in comparison to conventional techniques.

As shown in FIG. 3, the membrane thickness of the decellularized tissue in Example 1 was clearly smaller than the decellularized tissue in Comparative Example 4. In this manner, it can be confirmed that application of ultrahigh hydrostatic pressure in an aqueous solution containing a water-soluble polysaccharide enables a conspicuous inhibition of swelling. Moreover, since the decellularized tissue in Example 1 displays a higher overall transparency than the decellularized tissue in Comparative Example 4, it is clear that the transparency of the cornea is improved by application of ultrahigh hydrostatic pressure in an aqueous solution containing a water-soluble polysaccharide.
Degree of Decellularization A section of decellularized tissue prepared in the examples and comparative examples and a control section of cornea (unprocessed) prior to the application pressure used in the examples were stained using HE stain using a normal technique. FIG. 2 shows a photomicrograph of each tissue section after staining. The results are respectively shown in which (G) is a control, (H) is a comparative example using SDS, (I) is a comparative example using TritonX-100, (J) is a comparative example using sodium cholate, (K) is Example 1 and (L) is Example 2.

As shown in FIG. 2(G)-(J), stained spots can be observed in the decellularized tissue in the Comparative Examples and the control cornea and thereby it is clear that cells have not been sufficiently removed. In contrast, as shown in FIG. 2(K), (L), stained spots cannot be observed in the decellularized tissue in Example 1 and 2 and thereby it is clear that cells have been almost completely removed.

From the description above, it can be confirmed that decellularization performed by the application of ultrahigh hydrostatic pressure enables conspicuous inhibition of swelling and conspicuous improvement of safety.
Maintenance of Structure It is known that living corneal tissue maintains transparency when adjusted to a level of swelling of approximately 70% by the pump function of the corneal endothelial cells. Thus, if transparency is to be recovered when decellularized tissue of corneal origin contracts as a result of dehydration, there is a high possibility that transparency will be recovered by adjusting the level of swelling after transplantation and therefore this suggests the possibility of application as a graft.

Figure 4:
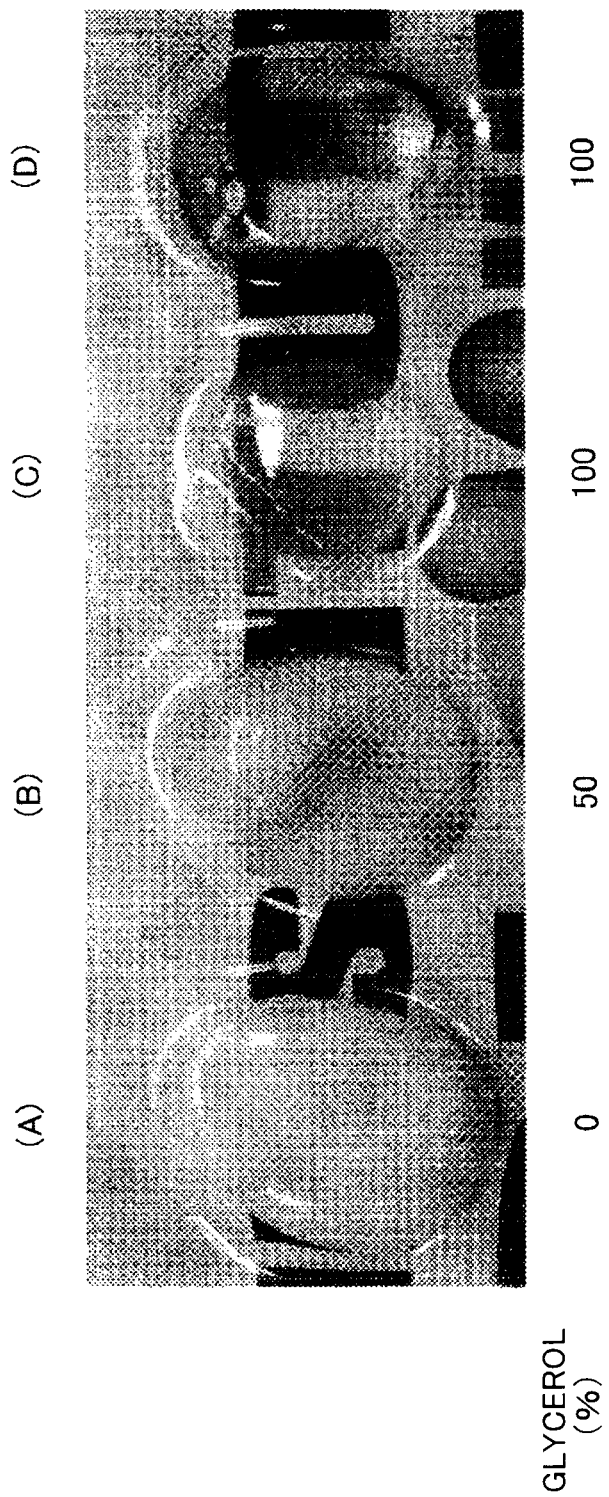
FIG. 4 shows transparency of decellularized tissue prepared using a preparation method according to an Example of the present invention.

A dehydration process was performed by immersing a control cornea and decellularized tissue prepared according to Example 2 for 24 hours in a 50% and 100% glycerol aqueous solution acting as a hypertonic solution. Thereafter the cornea and the decellularized tissue were observed. The results are shown in FIG. 4. (A) denotes the decellularized tissue before immersion, (B) denotes decellularized tissue after processing using a 50% glycerol aqueous solution, (C) denotes decellularized tissue after processing using a 100% glycerol aqueous solution, and (D) denotes cornea after processing using a 100% glycerol aqueous solution.

As shown in (A), the decellularized tissue before dehydration processing is white and turbid and has low transparency. In contrast, as shown in (B), (C), as dehydration progresses, the turbidity of the decellularized tissue is eliminated and transparency is recovered. Thus the decellularized tissue according to Example 2 suggests that structure is not disrupted and that as dehydration progresses naturally after transplantation, transparency can be recovered.

Figure 5:
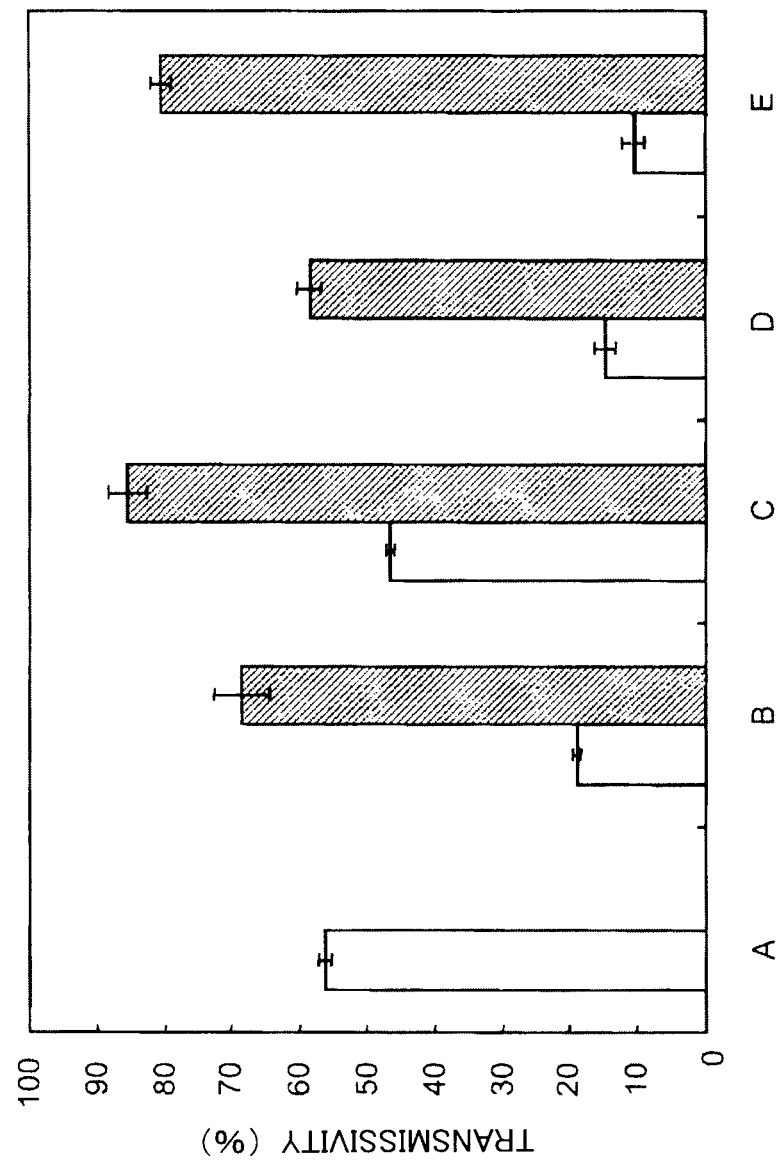
FIG. 5 is a graph showing transmissivity of decellularized tissue prepared using a preparation method according to an example of the present invention.

The transparency of each tissue was subjected to numerical conversion and compared. In other words, transmissivity was measured by measuring the absorbance at a wavelength of 600 nm before and after the decellularized tissue prepared in Examples 2 and 3 was subjected to a dehydration process by immersion for 72 hours in 100% glycerin aqueous solution. Controls were prepared respectively including cornea (control 1), the same corneal tissue immersed for 72 hours in PBS solution (control 2), and immersed in PBS solution containing 3.5 mass % dextran (control 3) and respective transmissivity was measured. The results are shown in FIG. 5. A denotes control 1, B denotes control 2, C denotes control 3, D denotes Example 3 and E denotes Example 4. The uncolored white bar shows transmissivity before the dehydration process and the shaded bar shows transmissivity after the dehydration process.

As shown in A, D, E, the transmissivity of both the decellularized tissue in Example 2 and in Example 3 after the dehydration process is confirmed to return to at least the same level as the cornea. Thus the decellularized tissue in Examples 2 and 3 suggests that structure is not disrupted and transmissivity can be recovered by natural dehydration after transplantation.

Figure 6:
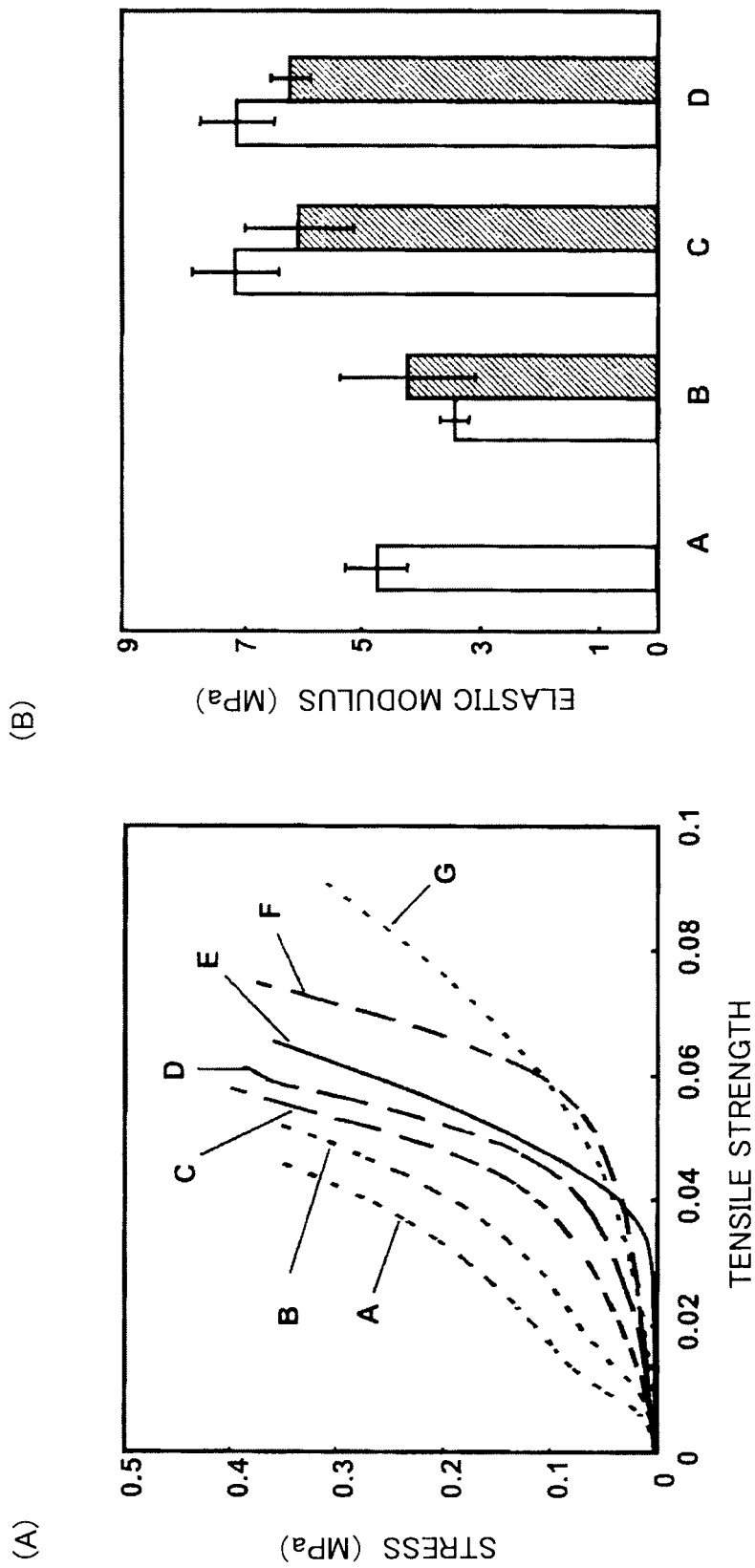
FIG. 6 is a graph showing mechanical properties of decellularized tissue prepared using a preparation method according to an example of the present invention.

Furthermore since Example 3 has a still higher transmissivity than Example 2, it suggests that use as a graft will be improved by application of a ultrahigh hydrostatic pressure at 30° C.
Mechanical Strength The mechanical properties of the decellularized tissue were evaluated. Firstly decellularized tissue prepared in Examples 2 and 3 and the same decellularized tissue immersed for 3 days in 50% glycerol solution and subjected to dehydration processing were respectively cut into strips of 3 mm width and 15 mm length. The stress on these grafts when applying various torsional loads was measured using a mechanical strength testing apparatus "Leona II" (Yamaden Co., Ltd.). Controls were prepared respectively including cornea (control 1), the same corneal tissue immersed for 72 hours in PBS solution (control 2), and control 2 immersed for 1 hour in 100 mass % glycerol (control 3). The relationship between tensile strength and stress was measured. The results are shown in FIG. 6(A). In FIG. 6(A), A denotes Example 3, B denotes Example 2, C denotes Example 3 after dehydration processing, D denotes Example 2 after dehydration processing, E denotes control 1, and G denotes control 2.

As shown in A-D, the decellularized tissue prepared in Examples 2 and 3 displays excellent stress and even after dehydration processing, displays stress which is higher than or equal to that of a cornea. These results suggest that after natural post-transplantation dehydration, a degree of strength which is equivalent to the cornea can be maintained.

Furthermore the thickness of the graft was measured and stress-strain characteristics were used to calculate an elastic modulus. The results are shown in FIG. 6(B). In FIG. 6(B), A denotes the control 1, B denotes the control 2, C denotes Example 3 and D denotes Example 2. The uncolored white bar shows the elastic modulus before the dehydration process and the shaded bar shows the elastic modulus after the dehydration process.

As shown in A-D, the decellularized tissue in Examples 2 and 3 displays an excellent elastic modulus and, even after the dehydration process, displays an elastic modulus which is higher than or equal to that of the cornea. These results suggest that after natural post-transplantation dehydration, an elastic modulus which is equivalent to the cornea can be maintained and the functions of a corneal substitute can be sufficiently displayed.

Clinical Trial 1

Figure 7:
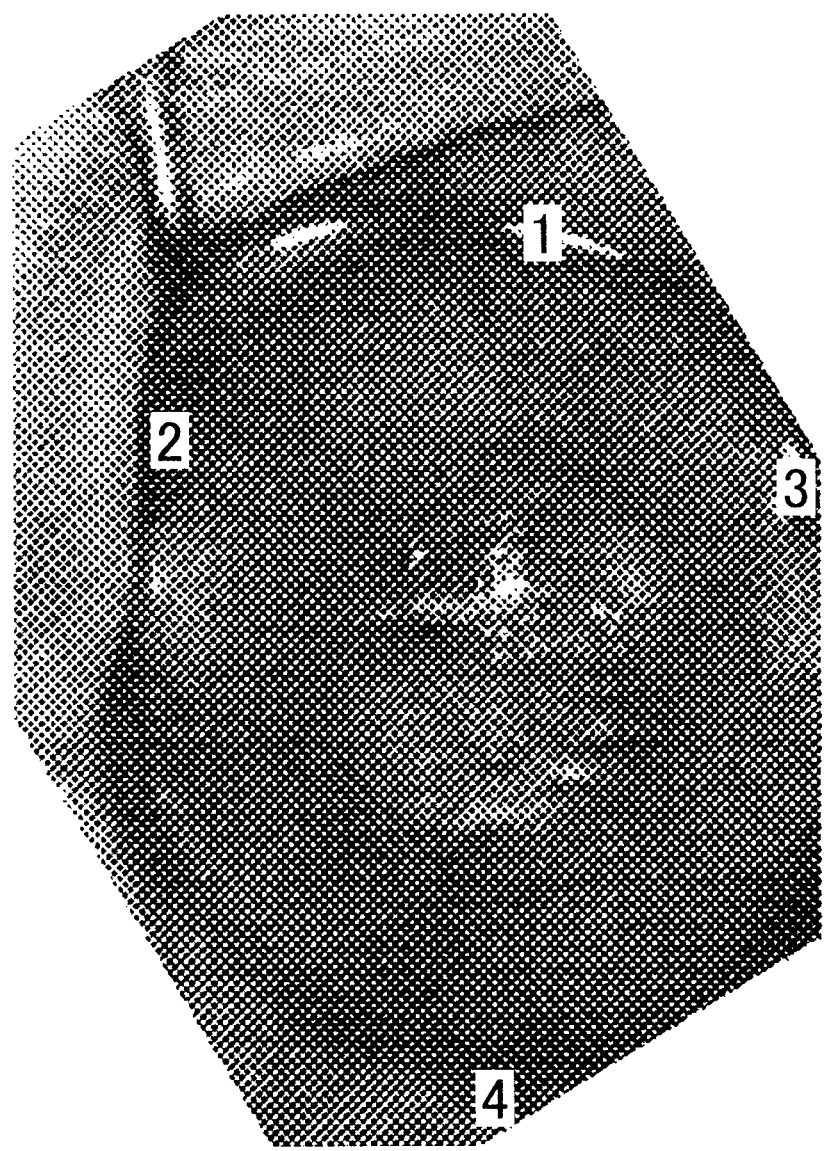
FIG. 7 shows a state immediately after a graft is transplanted according to an example of the present invention.
Figure 8:
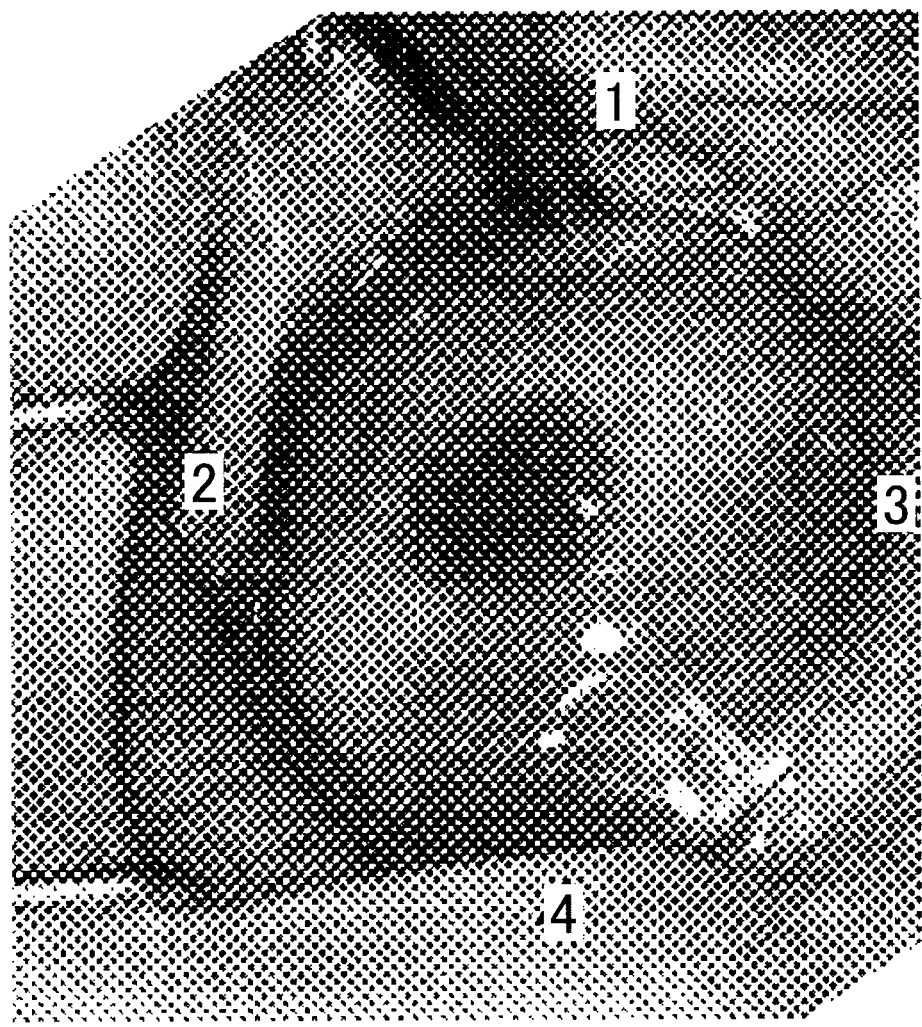
FIG. 8 shows a state eight weeks after a graft is transplanted according to an example of the present invention.

The parenchyma of a rabbit cornea was partially excised at four positions. The decellularized tissue prepared in Example 2 and the cornea used in Example 2 were cut into a size equal to that of the excised positions to prepare a graft. The various grafts were inserted into the excised positions to cover the remaining anterior epithelium of the cornea. The state of the rabbit eyeball at this time is shown in FIG. 7. Thereafter the state of the eyeball was observed again after an eight-week period of rearing the rabbit under normal conditions. The results are shown in FIG. 8. Corneal grafts were inserted into the excised positions shown by 1 and 4 in FIG. 7 and FIG. 8, and grafts of the decellularized tissue were inserted into the excised positions shown by 2 and 3.

As shown by FIG. 7 and FIG. 8, the excised positions 1, 4 having inserted corneal grafts were transparent after transplantation but become turgid by eight weeks after transplantation. On the other hand, although the excised positions 2, 3 having inserted grafts of decellularized tissue according to Example 2 were slightly turgid immediately after transplantation, they developed a transparency to a level equal to surrounding tissue by eight weeks after transplantation.

Figure 9:
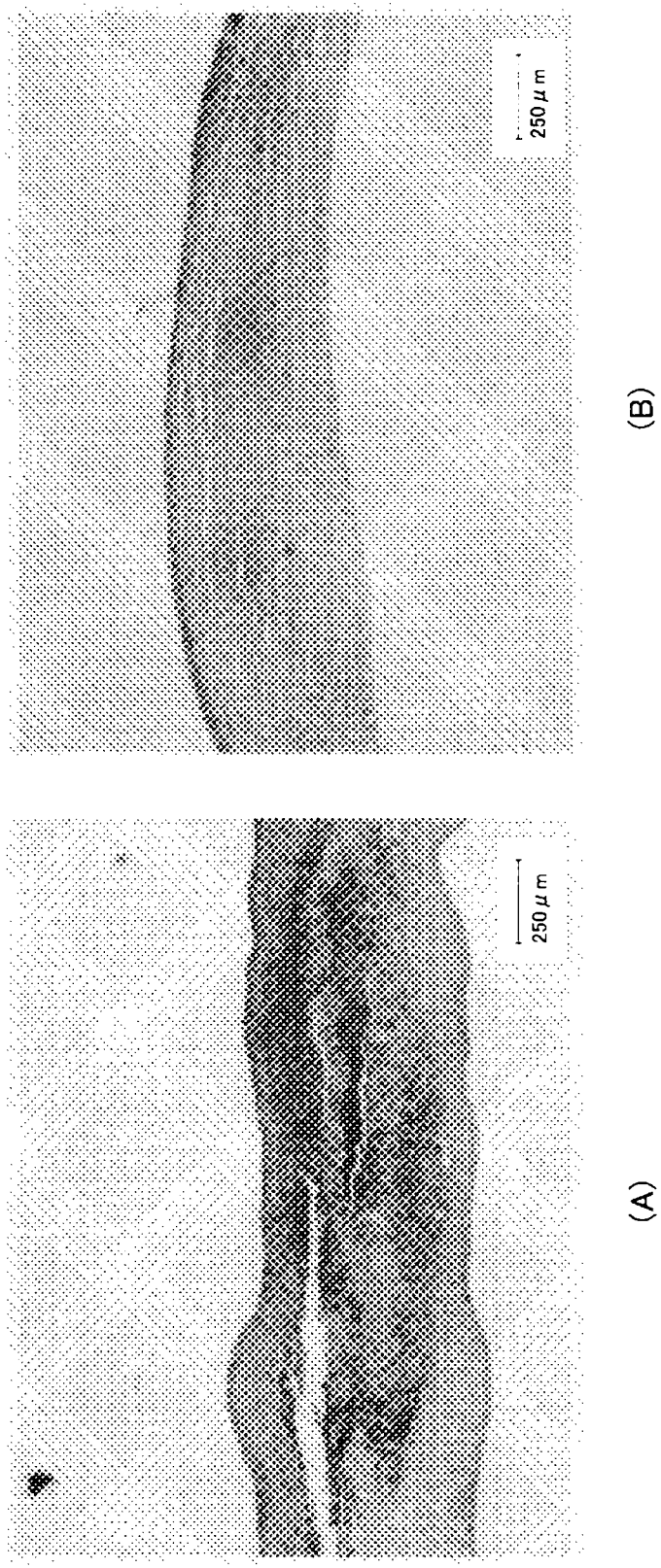
FIG. 9 shows an attachment state eight weeks after a graft is transplanted according to an example of the present invention.

At eight weeks after transplantation, the corneas were recovered and sectional surface of the excised positions 1 and 2 were stained using HE stain. FIG. 9 shows a photomicrograph after staining. In FIG. 9, A on the sectional surface denotes the excised position 1 and B denotes the excised position 2.

As shown in FIG. 9, numerous cells are observed to be moistened on the periphery of the inserted graft at excised position 1 clearly showing an active immunological reaction. In contrast, at excised position 2, almost no moistened cells can be observed in the periphery of the graft and the attachment of the graft to the peripheral tissue can be confirmed.

Clinical Trial 2

Figure 10:
FIG. 10 shows a regeneration state of contiguous tissue when a graft is transplanted according to an example of the present invention.
Figure 10:
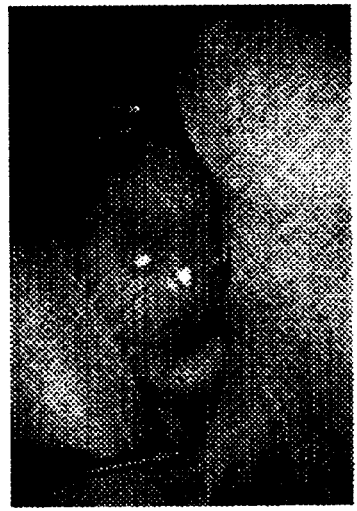
Figure 10:
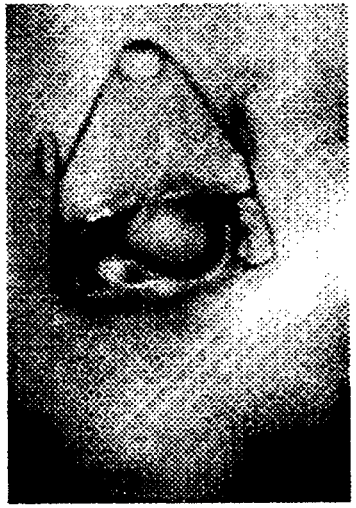
Figure 10:
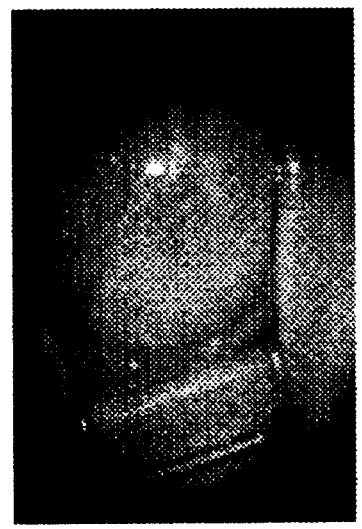
Figure 10:
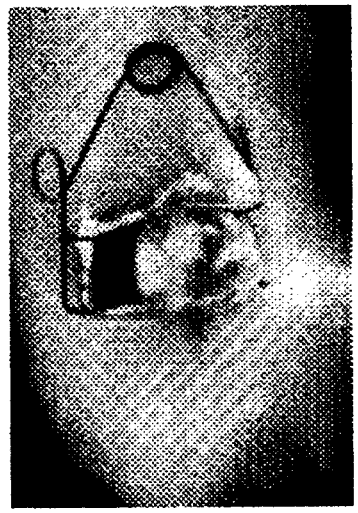
Figure 10:
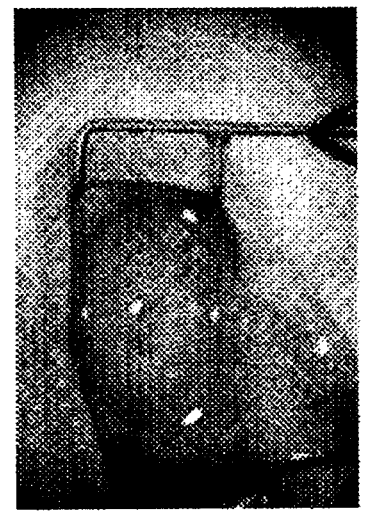

An experiment was performed using the same steps as those described in Clinical Trial 1 with the exception that the anterior epithelium of the cornea was not covered and the graft of the decellularized tissue was exposed. At one week, two weeks and three weeks after transplantation, fluorescein sodium was applied by dripping onto the eyeball using Florence test paper. Then the eyeball was observed under fluorescent illumination for 1-10 minutes. The fluorescent dye could not stain anterior epithelium of the cornea thus clearly showing that the parenchyma of the cornea could be stained. The results are shown in FIG. 10. After these observations, the test reagents were removed by washing with a physiological saline solution and the observation was repeated at weekly intervals. The lower row in FIG. 10 shows the results of observing the eyeball under visible light at one week, two weeks and three weeks after transplantation.

As shown by the upper row in FIG. 10, at one week after transplantation, although the graft was stained by fluorescent dye due to the absence of an epithelium, after two weeks, the position of the stained graft became limited and after three weeks, a stained position was almost not observable. These results prove that the decellularized tissue in Example 2 has properties enabling the regeneration of the anterior epithelium of the cornea which is a contiguous tissue.

As shown by the lower row in FIG. 10, the majority of eyeballs were turbid at one week after transplantation. However, after two weeks, the turbid site is of limited extent and after three weeks, the entire eyeball became transparent and phenomena such as vascular infiltration could be observed. These results prove that the decellularized tissue in Example 2 has properties enabling the recovery of transparency after transplantation.

The invention claimed is:

1. A method of preparing a decellularized soft tissue in which soft tissue of animal origin is decellularized, the method comprising:
    an application step of disrupting cells in the soft tissue by applying an ultrahigh hydrostatic pressure to an isolated soft tissue in a medium; and
    a removal step of removing the disrupted cells,
    wherein the medium is an aqueous solution containing a water-soluble polysaccharide;
    wherein the ultrahigh hydrostatic pressure is at least 1000 atmospheres,
    wherein the application step comprises a pressure limiting step of limiting the rate of pressure increase or pressure decrease in the applied pressure applied to the medium to inhibit solidification of the medium and damage to the structure of the decellularized tissue during the process of the pressure increase or pressure decrease by preventing the applied pressure applied to the medium from taking a value greater than or equal to a melt pressure of the medium that is calculated in advance based on the composition of the medium.

2. The method according to claim 1, wherein the water-soluble polysaccharide is at least one type of polysaccharide selected from a group consisting of dextran, alginic acid, hyaluronic acid, trehalose, 2-methacryloyloxyethyl phosphorylchloine, and polyvinylpyrrolidone.

3. The method according to claim 1, wherein the application step includes a temperature maintenance step of maintaining a temperature of the medium to be greater than or equal to a melting point of the medium at the ultrahigh hydrostatic pressure.

4. The method according to claim 1, wherein the soft tissue is corneal tissue.

* * * * *